US009643899B2

(12) United States Patent
Fickel

(10) Patent No.: US 9,643,899 B2
(45) Date of Patent: May 9, 2017

(54) SSZ-13 AS A CATALYST FOR CONVERSION OF CHLOROMETHANE TO OLEFINS

(71) Applicant: SABIC Global Technologies B.V., Bergen op Zoom (NL)

(72) Inventor: Dustin Fickel, Richmond, TX (US)

(73) Assignee: SABIC Global Technologies B.V., Bergen op Zoom (NL)

( * ) Notice: Subject to any disclaimer, the term of this patent is extended or adjusted under 35 U.S.C. 154(b) by 0 days.

(21) Appl. No.: 15/236,690

(22) Filed: Aug. 15, 2016

(65) Prior Publication Data

US 2017/0057886 A1    Mar. 2, 2017

Related U.S. Application Data

(60) Provisional application No. 62/209,097, filed on Aug. 24, 2015.

(51) Int. Cl.
| | | |
|---|---|---|
| C07C 1/00 | (2006.01) | |
| C08F 210/00 | (2006.01) | |
| C07C 1/30 | (2006.01) | |
| B01J 29/70 | (2006.01) | |
| B01J 29/90 | (2006.01) | |
| C08F 10/00 | (2006.01) | |

(52) U.S. Cl.
CPC ............. *C07C 1/30* (2013.01); *B01J 29/7015* (2013.01); *B01J 29/90* (2013.01); *C08F 10/00* (2013.01); *C07C 2529/70* (2013.01)

(58) Field of Classification Search
CPC . Y02P 20/52; C07C 2529/85; C07C 2529/89; C07C 11/06; C07C 11/04; C01B 37/02; C01B 37/08; C01B 37/04; B01J 29/7015; B01J 29/7038; B01J 29/7476; B01J 29/7676
USPC .......................................... 585/642; 526/348
See application file for complete search history.

(56) References Cited

U.S. PATENT DOCUMENTS

| | | | |
|---|---|---|---|
| 4,496,786 A | 1/1985 | Santilli et al. | 585/640 |
| 4,544,538 A | 10/1985 | Zones | 423/706 |
| 7,148,172 B2 | 12/2006 | Strohmaier et al. | 502/64 |
| 7,829,751 B2 | 11/2010 | Levin et al. | 585/640 |
| 2008/0103345 A1 | 5/2008 | Levin et al. | 585/640 |
| 2008/0159950 A1 | 7/2008 | Miller et al. | 423/704 |
| 2008/0188701 A1 | 8/2008 | Qi et al. | |

FOREIGN PATENT DOCUMENTS

WO    WO 03/078324    9/2003

OTHER PUBLICATIONS

Svelle et al., "The methyl halide to hydrocarbon reaction over H-SAPO-34", Journal of Catalysis, 241: 243-254, 2006.*
(Continued)

*Primary Examiner* — William Cheung
(74) *Attorney, Agent, or Firm* — Norton Rose Fulbright US LLP

(57) ABSTRACT

Disclosed are methods and systems for converting chloromethane to olefins. A method includes contacting an aluminosilicate catalyst having a chabazite zeolite structure with a feed that includes an alkyl halide and is substantially free of oxygenates under reaction conditions sufficient to produce an olefin hydrocarbon product comprising $C_2$-$C_4$ olefins.

20 Claims, 5 Drawing Sheets

(56) References Cited

OTHER PUBLICATIONS

International Search Report and Written Opinion for PCT/US2016/046969, mailed Nov. 18, 2016.
Deng et al., "The synthesis of SSZ-13 with mixed template and it's catalytic performance for methanol to olefins reaction", *2$^{th}$ International Conference on Electronic & Mechanical Engineering and Information Technology*, 2012.
Nilsen et al., "The conversion of chloromethane to light olefins over SAPO-34: The influence of dichloromethane addition", *Applied Catalysis A: General* 367 (2009) 23-31.
Wu et al., "Dual template synthesis of a highly mesoporous SSZ-13 zeolite with improved stability in the methanol-to-olefins reaction", *Chem Commun.*, 2012, 48, 9492-9494.
Bordiga et.al., "Assessing the Acidity of High Silica Chabazite H-SSZ-13 by FTIR Using CO as Molecular Probe: Comparison with H-SAPO-34", *J. Phys. Chem B*. 2005, 109, 2779-2784.
Jaumain et al., "Direct catalytic conversion of chloromethane to higher hydrocarbons over various protonic and cationic zeolite catalysts as studied by in-situ FTIR and catalytic testing", *Studies in Surface Science and Catalysis*, 130: 1607-1612, 2000.
Wei et al., "New route for light olefins production from chloromethane over HSAPO-34 molecular sieve", *Catalysis Today*, 106: 84-89, 2005.
Xu et al. "Fluoride-treated HZSM-5 as a highly selective stable catalyst for the production of propylene from methyl halides", *Journal of Catalysis*, vol. 295, Nov. 2012, pp. 232-241.

\* cited by examiner

SSZ-13 AS A CATALYST FOR CONVERSION OF CHLOROMETHANE TO OLEFINS

CROSS REFERENCE TO RELATED APPLICATIONS

This application claims the benefit of priority of U.S. Provisional Patent Application No. 62/209,097, filed Aug. 24, 2015, which is hereby incorporated by reference in its entirety.

BACKGROUND OF THE INVENTION

A. Field of the Invention

The invention generally concerns the use of aluminosilicate zeolite catalysts for the conversion of chloromethane to olefins. In particular, an aluminosilicate zeolite catalyst SSZ-13 having a chabazite zeolite structure can be used to convert an alkyl halide feed that is substantially free of oxygenates to light olefins.

B. Description of Related Art

Light olefins such as ethylene and propylene are used by the petrochemical industry to produce a variety of key chemicals that are then used to make numerous downstream products. By way of example, both of these olefins are used to make a multitude of plastic products that are incorporated into many articles and goods of manufacture. FIGS. 1A and 1B provide examples of products generated from ethylene (FIG. 1A) and propylene (FIG. 1B). Currently, the main process used to prepare light olefins is via steam cracking of naphtha. This process, however, requires large amounts of naphtha, which in-turn, is obtained from the distillation of crude oil. While this process is viable, its reliance on crude oil can be a rate-limiting step and can increase the manufacturing costs associated with ethylene and propylene production. Thus, other feed sources such as oxygenates and alkyl halides have been investigated as possible feedstocks.

Various publications have been directed to the use of zeolitic or aluminosilicate catalysts in oxygenate to olefin (OTO) processes such as methanol to olefin (MTO). By way of example, U.S. Pat. No. 7,148,172 to Strohmaier et al. describes a MTO process that can convert a feed that includes oxygenates (e.g., methanol or ethanol) and alkyl halides having 3 to 10 carbon atoms to olefins rich in ethylene and propylene by contacting the feed with a low acidity chabazite material (i.e., a silica and alumina with a molar ratio of silica to alumina in excess of 100, such as 265). However, due to the remaining acidic catalytic sites, dehydration or partial dehydration of methanol or $C_3$-$C_{10}$ alkyl halides is possible, and by-products such as di-olefins, dimethyl ether and formaldehyde can be formed. Another problem associated with MTO processes is that when the oxygenate-based feedstock contains ethanol, acetaldehyde (e.g., which is formed by selective dehydrogenation of ethanol) or other oxidized compounds can be formed as by-products. Under certain conditions, formaldehyde can further react to form methyl formate and, in some cases, hydrogen and carbon monoxide. To inhibit the formation of by-products when oxygenates are present, the MTO catalysts can be treated with dopants (e.g., metal oxides) to minimize the formation of acetaldehyde. By way of example, U.S. Pat. No. 7,829,751 to Levin et al. describes a methanol/ethanol process for producing olefins from an oxygenate feed that includes at least 5 wt. % ethanol in which the feed is contacted with a catalyst composition that includes an aluminosilicate catalyst and a basic metal oxide co-catalyst. The basic metal oxide co-catalyst is used to minimize the formation of oxygenate by-products (e.g., acetaldehyde).

Other methods to generate olefins that use alkyl halides as a feed source use silicoaluminophosphate zeolite catalysts (e.g., SAPO-34) or catalysts having a pentasil structure (e.g., ZSM-5). By way of example, Wei et al. in *New route for light olefins production from chloromethane over HSAPO-34 molecular sieve*, Catalysis Today, Vol. 106, October 2005, pp. 84-89 describes the use of a calcined HSAPO-34 zeolites to convert chloromethane to light olefins. However, these catalysts suffer from less than optimal selectivity to a desired olefin (e.g., propylene) and rapid catalyst deactivation. In Xu et al. in *Fluoride-treated HZSM-5 as a highly selective stable catalyst for the production of propylene from methyl halides*, Journal of Catalysis, Vol. 295, November 2012, pp. 232-241, calcined HZSM-5 catalysts were used and deactivated quickly. The catalysts required doping with fluoride to improve catalytic performance.

One of the problems seen with the currently available catalysts used to produce olefins is that such catalysts have relatively low catalyst activity. This results in an inefficient process that increases the time and expenses associated with producing olefin products. Still further many of the currently used processes rely on the presence of oxygenate compounds in the reaction feed, thereby further increasing production costs, and also introducing the possibility of the formation of unwanted by-products from said oxygenates.

SUMMARY OF THE INVENTION

A discovery has been made that provides a solution to some of the current problems associated with producing light olefins (e.g., $C_2$-$C_4$ olefins). The solution resides in the use of aluminosilicate zeolite catalysts having a chabazite zeolite structure that do not contain phosphorous atoms in their respective framework structures (e.g., SSZ-13). Without wishing to be bound by theory, it is believed that these types of catalysts contain acid sites of higher strength and are therefore more active when compared with traditional catalysts that are used to produce olefins (e.g., catalysts having phosphorous atoms in their framework structures such as silicoaluminophosphate (SAPO) catalysts (e.g., SAPO-34)). The increased acid site strength of the aluminosilicate zeolitic catalysts when compared with SAPO catalysts arises from the alumina species in the framework, which replaces a silica species in a tetrahedral environment. Whereas, for silicoaluminophosphates the acidity arises from inserting silica into a neutral aluminophosphate framework. The increased activity further allows for the use of feedstocks that are substantially free of oxygenates (e.g., alkyl halide feedstocks) to produce light olefins. As illustrated in non-limiting embodiments of the present invention, the catalysts of the present invention provide for a more efficient conversion of alkyl halides when compared with SAPO catalysts. Thus, the present invention offers a more efficient process for producing light olefins from alkyl halides. Further, the process of the present invention can be used with feedstocks that are substantially free of oxygenates, thereby reducing or avoiding the production of unwanted associated by-products.

In one aspect of the present invention, there is disclosed a method for converting an alkyl halide to an olefin using an aluminosilicate catalyst. The method includes contacting an aluminosilicate catalyst having a chabazite zeolite structure with a feed that includes an alkyl halide (e.g., a methyl halide) under reaction conditions sufficient to produce an olefin hydrocarbon product that includes $C_2$-$C_4$ olefins (e.g., ethylene, propylene, and butylene). The alkyl halide can be a methyl halide (e.g., methyl chloride, methyl bromide, methyl fluoride, or methyl iodide, or any combination thereof). In a preferred aspect, the methyl halide is methyl chloride. The feed can be substantially free of oxygenates (e.g., at least 50 wt. %, at least 75 wt. %, preferably at least 80 wt. %, and most preferably at least 90 wt. % alkyl halide). The feed stream includes less than 5 wt. % alcohol, preferably less than 1 wt. % alcohol, or preferably is alcohol free. When an alcohol is included in the feed stream, the alcohol can be methanol or ethanol. The aluminosilicate catalyst can have a $SiO_2/Al_2O_3$ (SAR) ratio of less than 100:1, preferably 5:1 to 100:1, more preferably 10:1 to 90:1, more preferably 20:1 to 80:1, or most preferably 40:1 to 80. In one instance, the SAR is 30:1 to 50:1 or preferably about 40:1, and in another instance, the SAR ratio is 65:1 to 85:1 or preferably about 76:1. The aluminosilicate catalyst used in the method can be SSZ-13. In one aspect, the reaction conditions of the method can include a temperature from 300° C. to 500° C., a pressure of 5 atm or less, and a weighted hourly space velocity (WHSV) of 0.5 to 10 $h^{-1}$. The combined maximum selectivity of ethylene and propylene can be at least 65% or 65% to 75% when the maximum combined space time yield of ethylene and propylene is at least 1/hr or 1/hr to 3/hr, and/or when the maximum conversion of alkyl halide is at least 70% or 80% to 100%. In some embodiments, the maximum selectivity of ethylene can be 50% to 70%. In certain embodiments, the maximum selectivity of propylene can be 60% to 80%. The method can further include collecting or storing the produced olefin hydrocarbon product. Also the methods include using the produced olefin hydrocarbon product to produce a petrochemical or a polymer. Still further, the method can include regenerating used/deactivated catalyst in a continuous process such as a fluid catalytic cracking (FCC)-type process or reactor or a circulating catalyst bed process or reactor.

In another aspect of the present invention, there is disclosed a system for producing olefins. The system includes an inlet for a feed that can include an alkyl halide; a reaction zone that is configured to be in fluid communication with the inlet; and an outlet configured to be in fluid communication with the reaction zone to remove an olefin hydrocarbon product from the reaction zone. The reaction zone can include the feed and an aluminosilicate catalyst having a chabazite zeolite structure. The reaction zone can be, or include, a fluid catalytic cracking (FCC)-type reactor or a circulating catalyst bed reactor. The system can further include a collection device that is capable of collecting the olefin hydrocarbon product. The feed used in the system can include at least 50 wt. %, at least 75 wt. %, preferably at least 80 wt. %, and most preferably at least 90 wt. % alkyl halide. The feed is substantially free of oxygenates (e.g., less than 5 wt. % oxygenates, preferably less than 1 wt. % oxygenates, or is oxygenate free). The feed stream can include less than 10 wt. %, more preferably less than 5 wt. %, and most preferably less than 1 wt. % or no alcohol. When an alcohol is included in the feed stream, the alcohol can be methanol or ethanol. The SAR of the catalyst can be less than 100:1 (e.g., 5:1 to 100:1, preferably, 5:1 to 100:1, more preferably 10:1 to 90:1, more preferably 20:1 to 80:1, or most preferably 40:1 to 80). The alkyl halide can be any alkyl halide described throughout the specification.

In the context of the present invention, embodiments 1 to 33 are disclosed. Embodiment 1 is a method for converting an alkyl halide to an olefin, the method comprising contacting an aluminosilicate catalyst having a chabazite zeolite structure with a feed comprising an alkyl halide under reaction conditions sufficient to produce an olefin hydrocarbon product comprising $C_2$-$C_4$ olefins, wherein the feed is substantially free of oxygenates. Embodiment 2 is the method of embodiment 1, wherein the feed comprises at least 50 wt. %, at least 75 wt. %, preferably at least 80 wt. %, and most preferably at least 90 wt. % alkyl halide. Embodiment 3 is the method of any one of embodiments 1 to 2, wherein the aluminosilicate catalyst has a silica ($SiO_2$) to alumina ($Al_2O_3$) ratio (SAR) of less than 100:1, preferably 5:1 to 100:1, more preferably 10:1 to 90:1, more preferably 20:1 to 80:1, or most preferably 40:1 to 80:1. Embodiment 4 is the method of embodiment 3, wherein the SAR is 30:1 to 50:1 or preferably about 40:1. Embodiment 5 is the method of embodiment 3, wherein the SAR ratio is 65:1 to 85:1 or preferably about 76:1. Embodiment 6 is the method of any one of embodiments 1 to 5, wherein the aluminosilicate catalyst is SSZ-13. Embodiment 7 is the method of any one of embodiments 1 to 6, wherein the feed stream includes less than 5 wt. %, preferably less than 1 wt. %, or preferably is alcohol free. Embodiment 8 is the method of embodiment 7, wherein the alcohol is methanol or ethanol. Embodiment 9 is the method of any one of embodiments 1 to 8, wherein the feed stream includes less than 5 wt. % oxygenates, preferably less than 1 wt. % oxygenates, or is oxygenate free. Embodiment 10 is the method of any one of embodiments 1 to 9, wherein the alkyl halide is a methyl halide. Embodiment 11 is the method of embodiment 10, wherein the methyl halide is methyl chloride, methyl bromide, methyl fluoride, or methyl iodide, or any combination thereof. Embodiment 12 is the method of embodiment 11, wherein the methyl halide is methyl chloride. Embodiment 13 is the method of any one of embodiments 1 to 12, wherein the reaction occurs in a fluid catalytic cracking (FCC) reactor or fluidized circulating bed reactor. Embodiment 14 is the method of any one of embodiments 1 to 13, wherein the reaction conditions include a temperature from 300° C. to 500° C., a pressure of 0.5 MPa or less, and a weighted hourly space velocity (WHSV) of 0.5 to 10 $h^{-1}$. Embodiment 15 is the method of embodiment 14, wherein the maximum combined selectivity of ethylene and propylene is at least 65% or 65% to 75%, wherein the maximum combined space time yield of ethylene and propylene is at least 1/hr or 1/hr to 3/hr, and/or wherein the maximum conversion of alkyl halide is at least 70% or 80% to 100%. Embodiment 16 is the method of embodiment 15, wherein the maximum selectivity of ethylene is 50% to 70% and the maximum selectivity of propylene is 60% to 80%. Embodiment 17 is the method of any one of embodiments 1 to 16, further comprising collecting or storing the produced olefin hydrocarbon product. Embodiment 18 is the method of any one of embodiments 1 to 17, further comprising using the produced olefin hydrocarbon product to produce a petrochemical or a polymer. Embodiment 19 is the method of any one of embodiments 1 to 18, further comprising regenerating used/deactivated catalyst in a continuous process such as a fluid catalytic cracking (FCC)-type process or reactor or a circulating catalyst bed process or reactor.

Embodiment 20 is a system for producing olefins, the system comprising an inlet for a feed comprising an alkyl halide, wherein the feed is substantially free of oxygenates; a reaction zone that is configured to be in fluid communication with the inlet, wherein the reaction zone comprises the feed and an aluminosilicate catalyst having a chabazite zeolite structure; and an outlet configured to be in fluid communication with the reaction zone to remove an olefin hydrocarbon product from the reaction zone. Embodiment 21 is the system of embodiment 20, wherein the reaction zone includes a fluid catalytic cracking (FCC)-type reactor or a circulating catalyst bed reactor. Embodiment 22 is the system of any one of embodiments 20 to 21, further comprising a collection device that is capable of collecting the olefin hydrocarbon product. Embodiment 23 is the system of any one of embodiments 20 to 22, wherein the feed comprises at least 50 wt. %, at least 75 wt. %, preferably at least 80 wt. %, and most preferably at least 90 wt. % alkyl halide. Embodiment 24 is the system of any one of embodiments 20 to 23, wherein the aluminosilicate catalyst has a silica ($SiO_2$) to alumina ($Al_2O_3$) ratio (SAR) of less than 100, preferably 5:1 to 100:1, more preferably 10:1 to 90:1, more preferably 20:1 to 80:1, or most preferably 40:1 to 80. Embodiment 25 is the system of embodiment 24, wherein the SAR is 30:1 to 50:1 or preferably about 40:1. Embodiment 26 is the system of embodiment 24, wherein the SAR ratio is 65:1 to 85:1 or preferably about 76:1. Embodiment 27 is the system of any one of embodiments 20 to 26, wherein the aluminosilicate catalyst is SSZ-13. Embodiment 28 is the system of any one of embodiments 20 to 27, wherein the feed stream includes less than 5 wt. % alcohol, preferably less than 1 wt. % alcohol, or preferably is alcohol free. Embodiment 29 is the system of embodiment 28, wherein the alcohol is methanol or ethanol. Embodiment 30 is the system of embodiments 20 to 29, wherein the feed stream includes less than 5 wt. % oxygenates, preferably less than 1 wt. % oxygenates, or is oxygenate free. Embodiment 31 is the system of any one of embodiments 20 to 30, wherein the alkyl halide is a methyl halide. Embodiment 32 is the system of embodiment 31, wherein the methyl halide is methyl chloride, methyl bromide, methyl fluoride, or methyl iodide, or any combination thereof. Embodiment 33 is the system of embodiment 32, wherein the methyl halide is methyl chloride.

The following includes definitions of various terms and phrases used throughout this specification.

The phrase "aluminosilicate catalyst having a chabazite zeolite structure" refers to catalysts that that do not include phosphorous atoms in the respective framework structures. A non-limiting example of such a catalyst is SSZ-13. By comparison, an example of a class of catalysts having a phosphorous atom in their framework structures is silicoaluminophosphates (SAPO) such as SAPO-34.

The term "catalyst" means a substance, which alters the rate of a chemical reaction. A catalyst may either increase the chemical reaction rate (i.e., a "positive catalyst") or decrease the reaction rate (i.e., a "negative catalyst"). Catalysts participate in a reaction in a cyclic fashion such that the catalyst is cyclically regenerated. "Catalytic" means having the properties of a catalyst.

The term "conversion" means the mole fraction (i.e., percent) of a reactant converted to a product or products.

The term "selectivity" refers to the percent of converted reactant that went to a specified product, for example, $C_2$ olefin selectivity is the percent of chloromethane that formed ethylene, $C_3$ olefin selectivity is the percent of chloromethane that formed propylene, and $C_4$ olefin selectivity is the percent of chloromethane that formed butylene. It follows logically that $C_2$-$C_4$ olefin selectivity is the percent of chloromethane that formed ethylene, propylene, and butylene. The "maximum" selectivity refers to the upper limit of converted reactant at specified conditions.

The term "about" or "approximately" are defined as being close to as understood by one of ordinary skill in the art. In one non-limiting embodiment, the terms are defined to be within 10%, preferably within 5%, more preferably within 1%, and most preferably within 0.5%.

The use of the words "a" or "an" when used in conjunction with any of the terms "comprising," "including," "containing," or "having" in the claims or the specification may mean "one", but it is also consistent with the meaning of "one or more," "at least one," and "one or more than one."

The terms "wt. %", "vol. %", or "mol. %" refers to a weight, volume, or molar percentage of a component, respectively, based on the total weight, the total volume of material, or total moles, that includes the component. In a non-limiting example, 10 grams of component in 100 grams of the material is 10 wt. % of component.

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The catalysts of the present invention can "comprise," "consist essentially of," or "consist of" particular ingredients, components, compositions, etc. disclosed throughout the specification. With respect to the transitional phase "consisting essentially of," in one non-limiting aspect, basic and novel characteristics of the catalysts of the present invention are their ability to selectively produce an olefin from chloromethane, and in particular, ethylene, propylene, and butylene, in high amounts.

Other objects, features and advantages of the present invention will become apparent from the following figures, detailed description, and examples. It should be understood, however, that the figures, detailed description, and examples, while indicating specific embodiments of the invention, are given by way of illustration only and are not meant to be limiting. Additionally, it is contemplated that changes and modifications within the spirit and scope of the invention will become apparent to those skilled in the art from this detailed description.

DETAILED DESCRIPTION OF THE INVENTION

Figure 1A:
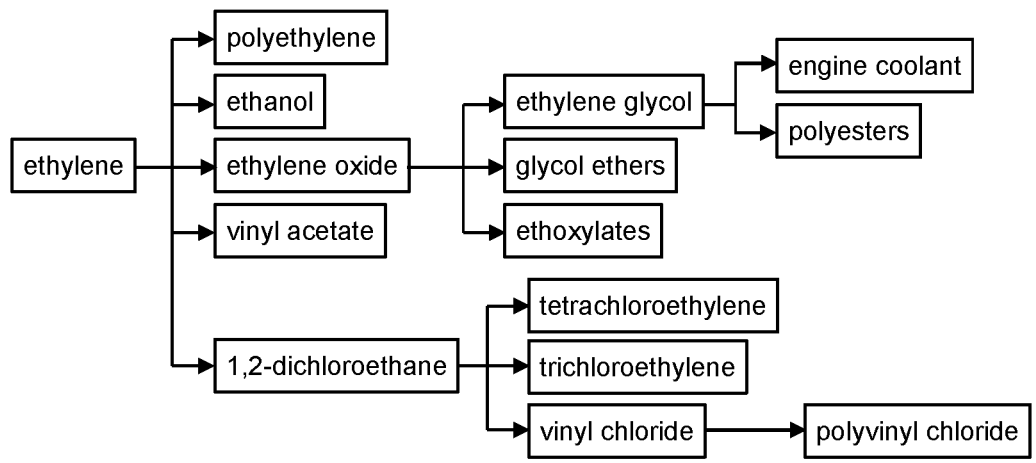
FIG. 1A is a chart of various chemicals and products that can be produced from ethylene.

A discovery has been made that solves the problems of producing $C_2$-$C_4$ olefins from alkyl halides feeds. The discovery is premised on the use of an acidic aluminosilicate zeolite catalyst. In particular, the discovery is premised on the use of an aluminosilicate zeolite catalyst having a chabazite zeolite (e.g., SSZ-13 type catalysts). It was surprisingly found that the aluminosilicate catalyst of the present invention had a higher chloromethane conversion and similar olefin selectivity as compared to a SAPO catalyst. While both catalyst have chabazite type structure, the catalysts have different acidities and activity. Thus, the catalysts have different performance properties towards alkyl halides. Without wishing to be bound by theory, it is believed this higher conversion is due to the aluminosilicate zeolite having a higher acidity than the silicoaluminophosphate catalyst. The higher acidity is believed to be due to the aluminum ions in the crystal structure instead of the silicon atoms, which are believed to provide the acidity for the silicoaluminophosphate catalysts.

These and other non-limiting aspects of the present invention are discussed in further detail in the following sections.

A. Aluminosilicate Catalysts

The aluminosilicate catalyst of the present invention has a chabazite (CHA) zeolite structure and belongs to the ABC-6 family of zeolites. Naturally occurring chabazite zeolites have a formula of $(Ca,Na_2,K_2,Mg)Al_2Si_4O_{12} \cdot 6H_2O$. Aluminosilicate catalysts that are isostructural with the chabazite mineral can be synthetically prepared. For example, a SSZ-13 is a synthetic CHA structure type aluminosilicate zeolite. SSZ-13 can be represented by the formula $RAl_{2.4}Si_{33.6}O_{72} \cdot wH_2O$ $(1.4<a<27)(0.7<b<4.3)$ $(1<w<7)$, where R is an organic templating or structure directing agent that is substantially removed upon calcination of the catalyst. Non-limiting examples of a templating agent include N is N,N,N-1-trimethyladamantammonium hydroxide, benzyltrimethyl ammonium hydroxide, choline chloride or the like. Such a SSZ-13 can have a SAR ratio 14:1. This SSZ-13 composition is not found in nature. The SSZ-13 catalysts and other aluminosilicate zeolite catalysts can be prepared using the procedure described in U.S. Pat. No. 4,496,786 or purchased from Zeolyst (USA), Johnson Matthey (USA), BASF (Germany), Tricat (Houston), Eurecat (France) Chevron (USA) or the like. A non-limiting example of a preparation of a synthetic aluminosilicate catalyst can include heating a solution of silica, aluminum sulfate or aluminum hydroxide, sodium hydroxide and deionized water, with N,N,N-trimethyl-1-adamantammonium hydroxide as a template at 160° C. for a desired amount of time (e.g., 4 days). The solution can be cooled to crystalize the zeolite in a CHA type structure. In the present invention, the aluminosilicate zeolite having a CHA structure can have a SAR of at least 100:1. In some aspects the SAR can range from 5:1 to 100:1, preferably from 10:1 to 90:1, more preferably from 20:1 to 80:1, or most preferably from 40:1 to 80:1, or 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, 25:1, 26:1, 27:1, 28:1, 29:1, 30:1, 31:1, 32:1, 33:1, 34:1, 35:1, 36:1, 37:1, 38:1, 39:1, 40:1, 41:1, 42:1, 43:1, 44:1, 45:1, 46:1, 47:1, 48:1, 49:1, 50:1, 51:1, 52:1, 53:1, 54:1, 55:1, 56:1, 57:1, 58:1, 59:1, 60:1, 61:1, 62:1, 63:1, 64:1, 65:1, 66:1, 67:1, 68:1, 69:1, 70:1, 71:1, 72:1, 73:1, 74:1, 75:1, 76:1, 77:1, 78:1, 79:1, 80:1, 81:1, 82:1, 83:1, 84:1, 85:1, 86:1, 87:1, 88:1, 89:1, 90:1, 91:1, 92:1, 93:1, 94:1, 95:1, 96:1, 97:1, 98:1, 99:1, or 100:1. In other aspects, the SAR can range from 30:1 to 50:1 or preferably about 40:1 or the SAR ratio can range from 65:1 to 85:1 or preferably about 76:1. Decreasing the SAR ratio to less than 100:1, increases the acidity or activity of the catalyst as compared to conventional SAPO-34 catalysts. In some embodiments, unmodified SSZ-13 is used, which is commercially available from at least the aforementioned sources. However, in other embodiments, modified SSZ-13 is used. While the SAR for each of the SSZ-13 zeolites can vary based on preparation, in preferred aspects, a SAR of at less than 100:1 for the aluminosilicate zeolite catalysts is preferred. In other aspects, the catalyst can be calcined to an H-form or commercially obtained. For example, the catalyst can be heated at a temperature 500 to 600° C., 510 to 590° C., 520 to 580° C., 530 to 570° C., 540 to 560° C., or 550° C. for about 2 to 10 hours, or 8 hours.

The relatively small pore diameter of SSZ-13 molecular sieves catalysts enables the higher selective formation of $C_2$-$C_4$ hydrocarbons as the molecules larger than the pore opening of molecular sieve are inhibited from exiting the zeolite framework/structure. The pore diameter of aluminosilicate catalyst in the current invention can range from about 3.7 Å to about 4 Å. For SSZ-13, the pore size is about 3.72 Å×3.72 Å. Similarly, the pore volume of the aluminosilicate catalyst can be 0.20 to 0.4 ml/g, 0.25 to 0.35 ml/g, 0.27 to 0.32 ml/g, or about 0.29 ml/g.

In certain aspects, the aluminosilicate zeolite catalyst of the present invention is acidic or a Brønsted-Lowry acid as defined by Arrhenius theory. (See, for example Bordia et. al., *J. Phys. Chem B.* 2005, 109, 2279-2784). A SAPO-34 catalyst and a SSZ-13 both have two acidic sites as determined using ammonia-temperature programmed desorption analysis. As shown in the Examples section, the SAPO-34 catalyst desorbs at lower temperatures than the SSZ-13 catalyst (e.g., SAPO-34 at 173° C. and 371° C., SSZ-13 at 175° C. and 440° C.). Without wishing to be bound by theory, it is believed that the higher desorption temperature correlates to stronger acid sites or higher activity.

In some aspects of the invention, the aluminosilicate zeolite catalyst can include other metals as dopants. Non-limiting examples of dopants include copper (Cu), nickel (Ni), iron (Fe), zinc (Zn), manganese (Mn), and molybdenum (Mo). Dopants can be added to the catalyst using known dopant techniques, for example, impregnation, ion exchange, chemical deposition or the like. An amount of dopant can depend inter alia on the desired activity of the catalyst. In some embodiments, the amount of dopant can range from 0.00001 wt. % to 0.05 wt. %.

B. Alkyl Halide Feed

The alkyl halide feed can include one or more alkyl halides. The alkyl halide feed may contain alkyl mono halides, alkyl dihalides, alkyl trihalides, preferably alkyl mono halide with less than 10% of other halides relative to the total halides. The alkyl halide feed may also contain nitrogen, helium, steam, and so on as inert compounds. The alkyl halide in the feed may have the following structure: $C_nH_{(2n+2)-m}X_m$, where n and m are integers, n ranges from 1 to 5, preferably 1 to 3, even more preferably 1, m ranges 1 to 3, preferably 1, X is Br, F, I, or Cl. In some aspects, the feed includes at least 50 wt. % alkyl halide under reaction conditions sufficient to produce an olefin hydrocarbon product comprising $C_2$-$C_4$ olefins. In other aspects, the feed may include at least 75 wt. %, preferably at least 80 wt. %, and most preferably at least 90 wt. % alkyl halide. Non-limiting examples of alkyl halides include methyl chloride, methyl bromide, methyl fluoride, or methyl iodide, or any combination thereof. In preferred aspects, the methyl halide is chloromethane. In a particular aspect, the feed includes less than 10 wt. % oxygenated compounds (e.g., alcohols), more preferably less than 5 wt. % oxygenates, and most preferably less than 1 wt. %, or 9 wt. %, 8 wt. %, 7 wt. %, 6 wt. %, 5 wt. %, 4 wt. %, 3 wt. %, 2 wt. %, 1 wt. %, 0.9 wt. %, 0.8 wt. %, 0.7 wt. %, 0.6 wt. %, 0.5 wt. %, 0.4 wt. %, 0.3 wt. %, 0.2 wt. %, 0.1 wt. %, 0.05 wt. % or 0.01 wt. % oxygenates or substantially none or no oxygenates. If oxygenates are present in the stream, they can be methanol, ethanol, or both.

The production of alkyl halide, particularly of chloromethane is commercially produced by thermal chlorination of methane at 400° C. to 450° C. and at a raised pressure. Catalytic oxychlorination of methane to methyl chloride is also known. In addition, methyl chloride is industrially made by reaction of methanol and HCl at 180° C. to 200° C. using a catalyst. Alternatively, methyl halides are commercially available from a wide range of sources (e.g., Praxair, Danbury, Conn.; Sigma-Aldrich Co. LLC, St. Louis, Mo.; BOC Sciences USA, Shirley, N.Y.). In preferred aspects, methyl chloride and methyl bromide can be used alone or in combination.

C. Olefin Production

The aluminosilicate (e.g., SSZ-13) catalysts of the present invention catalyze the conversion of alkyl halides to $C_2$-$C_4$ olefins such as ethylene, propylene and butylene. Reaction scheme (1) is an example of conversion of methyl chloride to ethylene, propylene and butylene using SSZ-13.

$$9CH_3X \xrightarrow{SSZ-13} C_2H_4 + C_3H_6 + C_4H_8 + 9HX \quad (2)$$

where X is Br, F, I, or Cl. Besides the $C_2$-$C_4$ olefins, the reaction may produce some byproducts such as methane, $C_5$ olefins, $C_2$-$C_5$ alkanes and aromatic compounds such as benzene, toluene and xylene. The produced haloacid can be separated from the olefin product stream and used in other downstream processes. For example, HCL can be generated from an alkyl halide. The HCl can be separated from the olefin product and provided to an oxyhydrochlorination unit. In an oxyhydrochlorination, the HCl can be reacted with methane and oxygen to produce chloromethane and water. The produced chloromethane can then the feed for the production of olefins, thereby, providing usage for all the chlorine produced in the reaction.

Conditions sufficient for olefin production (e.g., ethylene, propylene and butylene as shown in Equation 2) include temperature, time, alkyl halide concentration, space velocity, and pressure. The temperature range for olefin production may range from about 200° C. to 600° C., preferably ranging 300° C. to 500° C. In more preferred aspects, the temperature range is from 350° C. to 450° C. A weight hourly space velocity (WHSV) of alkyl halide higher than 0.5 h$^{-1}$ can be used, preferably between 0.5 and 10 h$^{-1}$, more preferably between 0.5 and 5 h$^{-1}$, even more preferably between 0.5 to 3 h$^{-1}$, or 0.5 h$^{-1}$, 1 h$^{-1}$, 1.5 h$^{-1}$, 2 h$^{-1}$, 2.5 h$^{-1}$, 3 h$^{-1}$. The conversion of alkyl halide to olefins can be performed at a pressure less than 1.4 MPa (200 psig) preferably less than 0.7 MPa (100 psig), more preferably less than 0.3 MPa (50 psig), even more preferably less than 0.14 MPa (20 psig). The pressure employed in the current invention can also be performed at 0.101 MPa or atmospheric conditions. Typically, the conditions for olefin production may be varied based on the type of the reactor. The method can further include collecting or storing the produced olefin hydrocarbon product along with using the produced olefin hydrocarbon product to produce a petrochemical or a polymer.

D. Catalyst Activity/Selectivity

Catalytic activity as measured by alkyl halide conversion can be expressed as the % moles of the alkyl halide converted with respect to the moles of alkyl halide fed. In particular aspects, the combined maximum selectivity of ethylene, propylene and butylene is at least 85% under certain reaction conditions. As individual products, the ethylene maximum selectivity can range from 30% to 55% and the propylene maximum selectivity ranging from 20% to 35%. The combined maximum selectivity of ethylene and propylene is at least 65% or 65% to 75% at 5 hours, or 66%, 67%, 68%, 69%, 70%, 71%, 72%, 73%, 74%, or 75%. In some aspects, a maximum selectivity $C_4$ alkenes is 0 to 15%, 0 to 10%, or 0 to 5% of $C_4$ alkenes, or 0%, 1%, 2%, 3%, 4%, 5%, 6%, 7%, 8%, 9%, 10%, 11%, 12%, 13%, 14%, or 15% of $C_4$ alkenes. Non-limiting examples of $C_4$-alkenes include trans-2-butene, cis-2-butene, and isobutene. Still further, the maximum selectivity of aromatic compounds produced during the process is less than 1% or less than 0.5% (e.g., 0.9%, 0.8%, 0.7%, 0.6%, 0.5%, 0.4%, 0.3%, 0.2%, 0.1% or less), and the maximum selectivity of $C_2$-$C_4$ alkanes is less than about 2% or less than 1% (e.g., 1.9%, 1.8%, 1.7%, 1.6%, 1.5%, 1.4%, 1.3%, 1.2%, 1.1%, 1.0%, 0.9%, 0.8%, 0.7%, 0.6%, 0.5%, 0.4%, 0.3%, 0.2%, 0.1% or less) under certain reaction conditions. As an example, chloromethane (CH$_3$Cl) is used here to define conversion and maximum selectivity of products by the following formulas:

$$\% \ CH_3Cl \ Conversion = \frac{(CH_3Cl)° - (CH_3Cl)}{(CH_3Cl)°} \times 100$$

where, (CH$_3$Cl)° and (CH$_3$Cl) are moles of methyl chloride in the feed and reaction product, respectively.

Maximum selectivity is defined as C-mole % and are defined for ethylene, propylene, and so on as follows:

$$\% \ Ethylene \ Selectivity = \frac{2(C_2H_4)}{(CH_3Cl)° - (CH_3Cl)} \times 100,$$

where the numerator is the carbon adjusted mole of ethylene and the denominator is the moles of carbon converted.

Maximum selectivity for propylene may be expressed as:

$$\% \ Propylene \ Selectivity = \frac{3(C_3H_6)}{(CH_3Cl)° - (CH_3Cl)} \times 100,$$

where the numerator is the carbon adjusted mole of propylene and the denominator is the moles of carbon converted.

Maximum selectivity for butylene may be expressed as:

$$\% \ Butylene \ Selectivity = \frac{4(C_4H_8)}{(CH_3Cl)° - (CH_3Cl) \ldots} \times 100,$$

where the numerator is the carbon adjusted mole of butylene and the denominator is the moles of carbon converted.

Selectivity for aromatic compounds may be expressed as:

$$\% \ Aromatics \ Selectivity = \frac{6(C_6H_6) + 7(C_7H_8) + 8(C_8H_{10})}{(CH_3Cl)° - (CH_3Cl) \ldots} \times 100,$$

where the numerator is the carbon adjusted moles of aromatics (benzene, toluene and xylene) and the denominator is the moles of carbon converted.

E. Olefin Production System

Figure 1B:
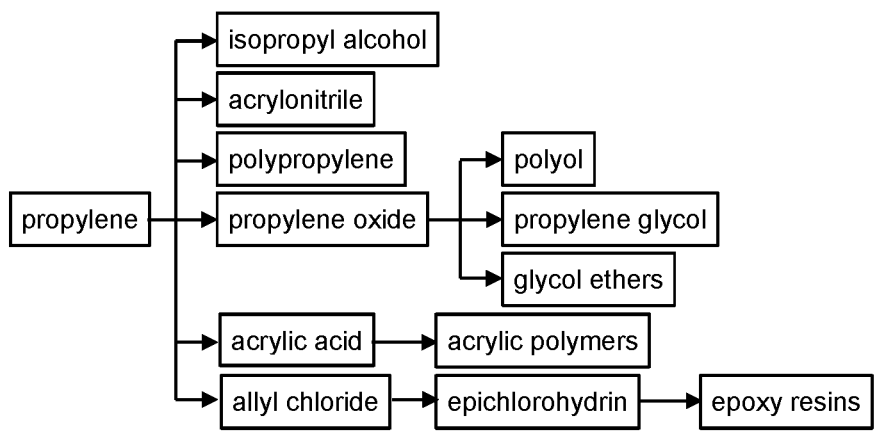
FIG. 1B is a chart of various chemicals and products that can be produced from propylene.
Figure 2:
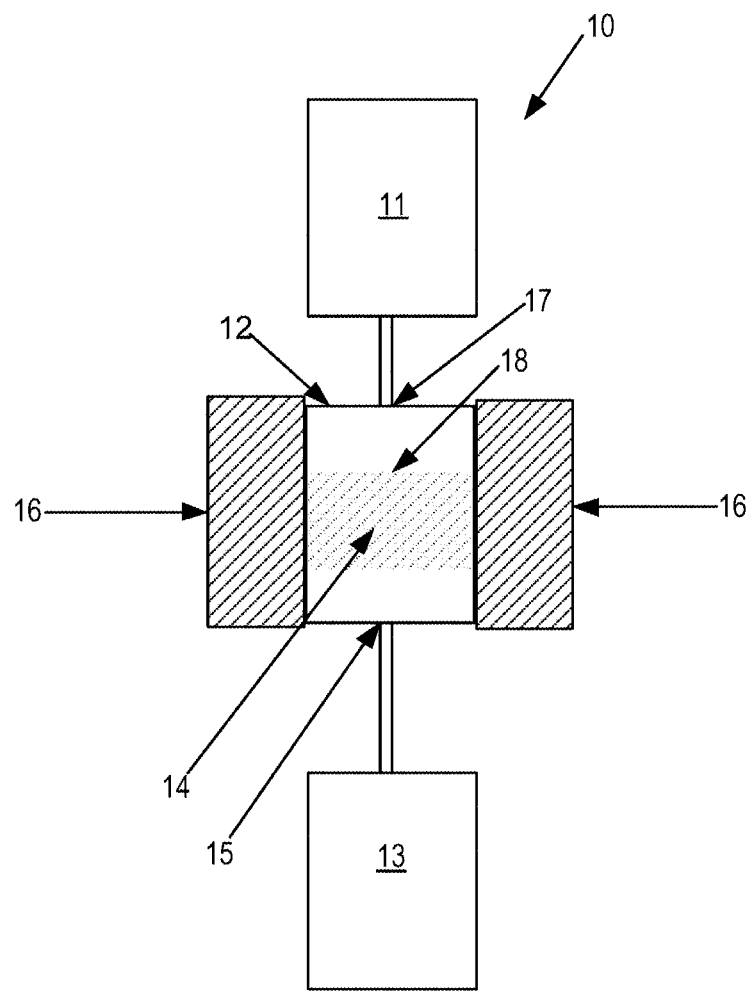
FIG. 2 is a schematic of an embodiment of a system for producing olefins from chloromethane.

Referring to FIG. 2, a system 10 is illustrated, which can be used to convert alkyl halides to olefin hydrocarbon products with the aluminosilicate zeolite catalysts having a chabazite zeolitic structure (e.g., SSZ-13) of the present invention. The system 10 can include an alkyl halide source 11, a reactor 12, and a collection device 13. The alkyl halide source 11 can be configured to be in fluid communication with the reactor 12 via an inlet 17 on the reactor. The amounts of the alkyl halide feed 11 and the catalyst 14 used can be modified as desired to achieve a given amount of product produced by the system 10. As explained above, the alkyl halide source can be configured such that it regulates the amount of alkyl halide feed entering the reactor 12. The reactor 12 can include a reaction zone 18 having the SSZ-13 zeolite catalyst 14 of the present invention. Non-limiting examples of reactors that can be used include fixed-bed reactors, fluidized bed reactors, bubbling bed reactors, slurry reactors, rotating kiln reactors, or any combinations thereof when two or more reactors are used. In a commercial process, reactor 12 is a fluidized bed reactor with a catalyst regenerator unit. The reactor 12 can include an outlet 15 for products produced in the reaction zone 18. The products produced can include ethylene, propylene and butylene. The collection device 13 can be in fluid communication with the reactor 12 via the outlet 15. Both the inlet 17 and the outlet 15 can be open and closed as desired. The collection device 13 can be configured to store, further process, or transfer desired reaction products (e.g., $C_2$-$C_4$ olefins) for other uses. The alkyl halide can enter reaction zone 18 via inlet 17 and contact the chabazite zeolitic structure (e.g., SSZ-13) to produce the desired olefinic reaction product. The desired reaction products exit the reaction zone 18 via outlet 15. By way of example only, FIG. 1 provides non-limiting uses of propylene and ethylene produced from the catalysts and processes of the present invention. Still further, the system 10 can also include a heating source 16. The heating source 16 can be configured to heat the reaction zone 18 to a temperature sufficient (e.g., 300 to 500° C.) to convert the alkyl halides in the alkyl halide feed to olefin hydrocarbon products. A non-limiting example of a heating source 16 can be a temperature controlled furnace. Additionally, any unreacted alkyl halide can be recycled and included in the alkyl halide feed to further maximize the overall conversion of alkyl halide to olefin products. Further, certain products or byproducts such as $C_5$+ olefins and $C_2$+ alkanes can be separated and used in other processes to produce commercially valuable chemicals (e.g., propylene). This increases the efficiency and commercial value of the alkyl halide conversion process of the present invention.

EXAMPLES

The present invention will be described in greater detail by way of specific examples. The following examples are offered for illustrative purposes only, and are not intended to limit the invention in any manner. Those of skill in the art will readily recognize a variety of noncritical parameters, which can be changed or modified to yield essentially the same results.

Example 1

Catalyst Preparation

SSZ-13 catalysts having the gel composition: Si:K:R: $H_2O$:$Al_2$ of 102:9:28:870:1 was synthesized in the following manner. N,N,N, trimethyl-1-adamantylammonium hydroxide (41.34 g, 25%) was mixed with KOH (0.97 g). Aluminum sulfate octadecahydrate (1.16 g, 98%) was added to the mixture while stirring. De-ionized water (80.3 g) was also added in order to dilute the mixture. Colloidal silica, (Ludox AS-40, 26.28 g, 40% Sigma-Aldrich®) was, then added to the mixture while stirring and the resulting mixture was allowed to keep stirring for an additional 45 minutes. The resulting gel was loaded into a Teflon lined autoclave and heated to 160° C. for 5 days under stirring (60 rpm). After crystallization was complete, the product was filtered and washed with 3 L of de-ionized water and then dried overnight (90° C.). The zeolite powder was calcined at 550° C. for 7 hours and then analyzed by powder x-ray diffraction to confirm the CHA structure.

Example 2

Catalyst Acidity Characterization

The acidity of SSZ-13 and SAPO-34 were each measured using ammonia-temperature programmed desorption analysis using 5% $NH_3$ in He at a flow rate of 50 cc/min for calibration and a measure flow rate of 50.04 $cm^3$ STP/min. Tables 1 and 2 provide the peak numbers, temperature (C.°) at maximum peak height, quantity ($cm^3$/g STP), and peak concentrations in percent for SSZ-13 and SAPO-34, respectively.

TABLE 1

(SSZ-13)

| Peak Number | Temperature at Maximum (° C.) | Quantity ($cm^3$/g STP) | Peak Concentration (%) |
|---|---|---|---|
| 1 | 176.53 | 3.38 | 0.18 |
| 2 | 441.06 | 6.71 | 0.12 |

TABLE 2

(SAPO-34)

| Peak Number | Temperature at Maximum (° C.) | Quantity ($cm^3$/g STP) | Peak Concentration (%) |
|---|---|---|---|
| 1 | 173.84 | 8.67 | 0.44 |
| 2 | 371.39 | 20.25 | 0.50 |

Example 3

Methyl Chloride Conversion to Olefins at 450° C., and 0 MPa

Each of the SSZ-13 Catalysts A and B of the present invention and the comparative catalyst SAPO-34 were tested for chloromethane conversion by using a fixed-bed tubular reactor at about 450° C. for a period of about 10 h or longer. For catalytic tests, the powder catalyst was pressed and then crushed and sized between 20 and 40 mesh screens. In each test a fresh load of sized (20-40 mesh) catalyst (1.0 g) was loaded in a stainless steel tubular (½-inch outer diameter) reactor. The catalyst was dried at 200° C. under $N_2$ flow (100 $cm^3$/min) for an hour and then temperature was raised to 450° C. at which time $N_2$ was replaced by methyl chloride feed (90 $cm^3$/min) containing 20 mol % $CH_3Cl$ in $N_2$. The weight hourly space velocity (WHSV) of $CH_3Cl$ was about 0.8 h$^{-1}$ to 3.0 h$^{-1}$ and reactor inlet pressure was about 0 MPa. The SAR, percent CH$_3$Cl conversion, turn over frequency (TOF), C$_2$ percent selectivity, C$_3$ percent selectivity of the catalysts of present invention (SSZ-13 catalysts A-C), and the Comparative SAPO-34 catalyst are listed in shown in Table 3. Selectivities were based on chloromethane and are carbon-based.

TABLE 3

| | | Taken at maximum Space Time Yield (STY) | | | | |
|---|---|---|---|---|---|---|
| Sample | SAR | Conversion (%) | TOF | C$_2$ Selectivity (%) | C$_3$ Selectivity (%) | STY[1] | C$_2$-C$_3$ Yield (%) |
| A | 76.0 | 99.65 | 2.69 | 51.97 | 21.94 | 1.27 | 73.64 |
| B | 40.0 | 98.93 | 2.67 | 34.95 | 33.99 | 1.27 | 68.20 |
| Comparative | 0.36 | 89.89 | 2.43 | 45.15 | 41.25 | 1.44 | 77.67 |

[1]STY: Tonnes [C2= + C3=]/Tonnes Cat/hr, WHSV = 2.7 and pressure was 0 MPa.

Figure 3:
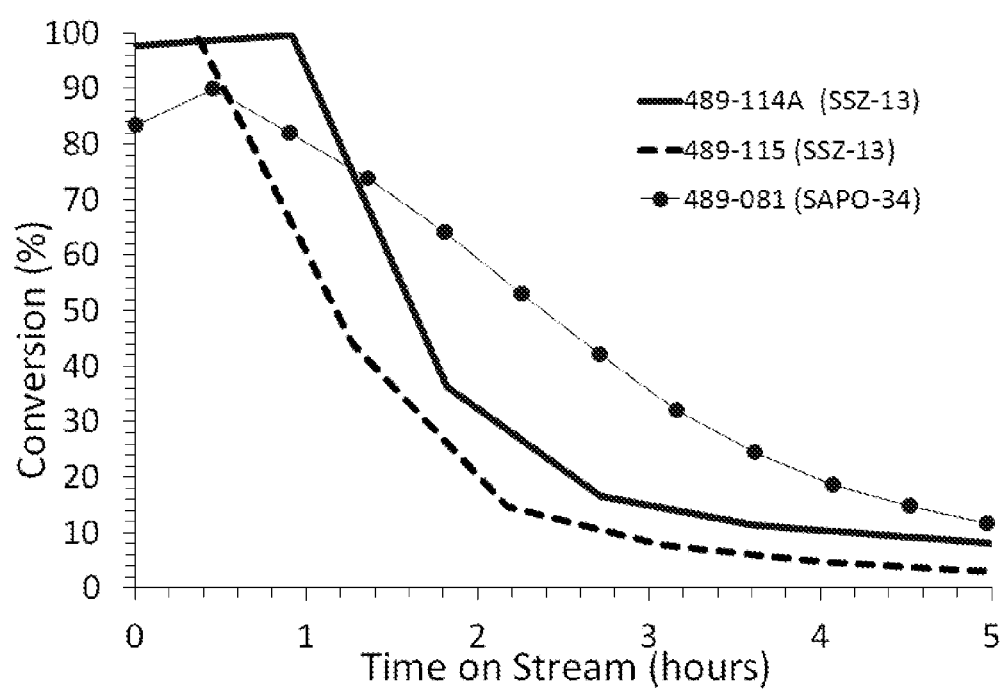
FIG. 3 is a graphical representation showing percent conversion of chloromethane the time on stream in hours for catalysts of the present invention and a SAPO-34 catalyst.
Figure 4:
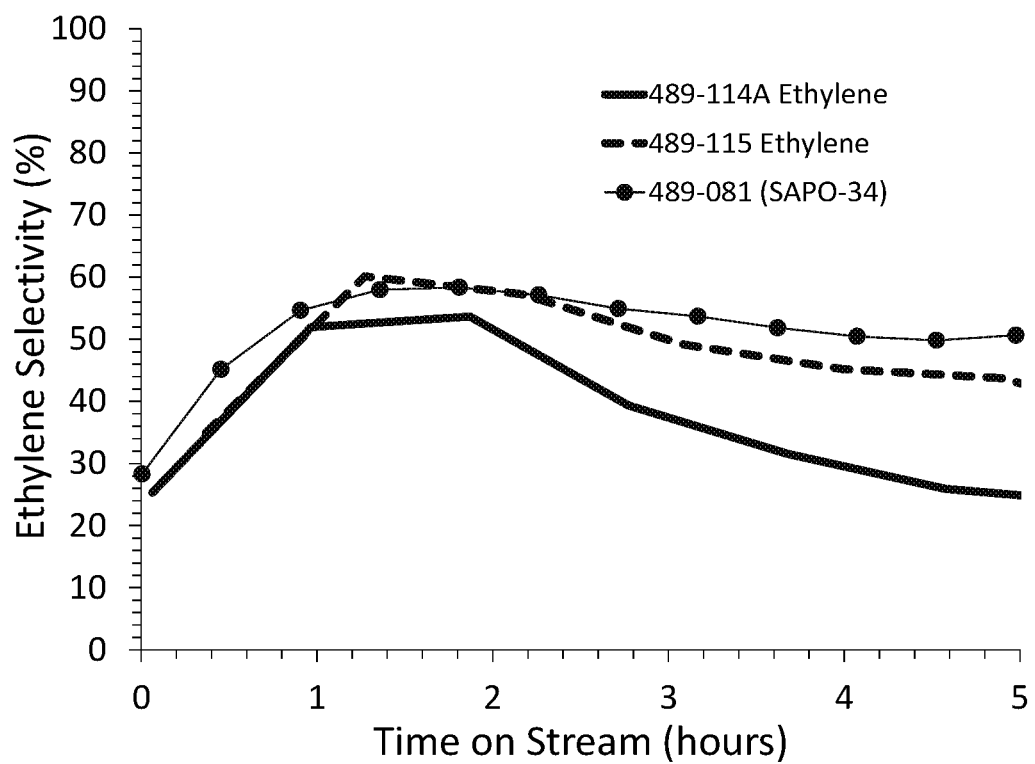
FIG. 4 is a graphical representation showing selectivity of ethylene and propylene formation in percentage versus the time on stream in hours for catalyst of the present invention.
Figure 5:
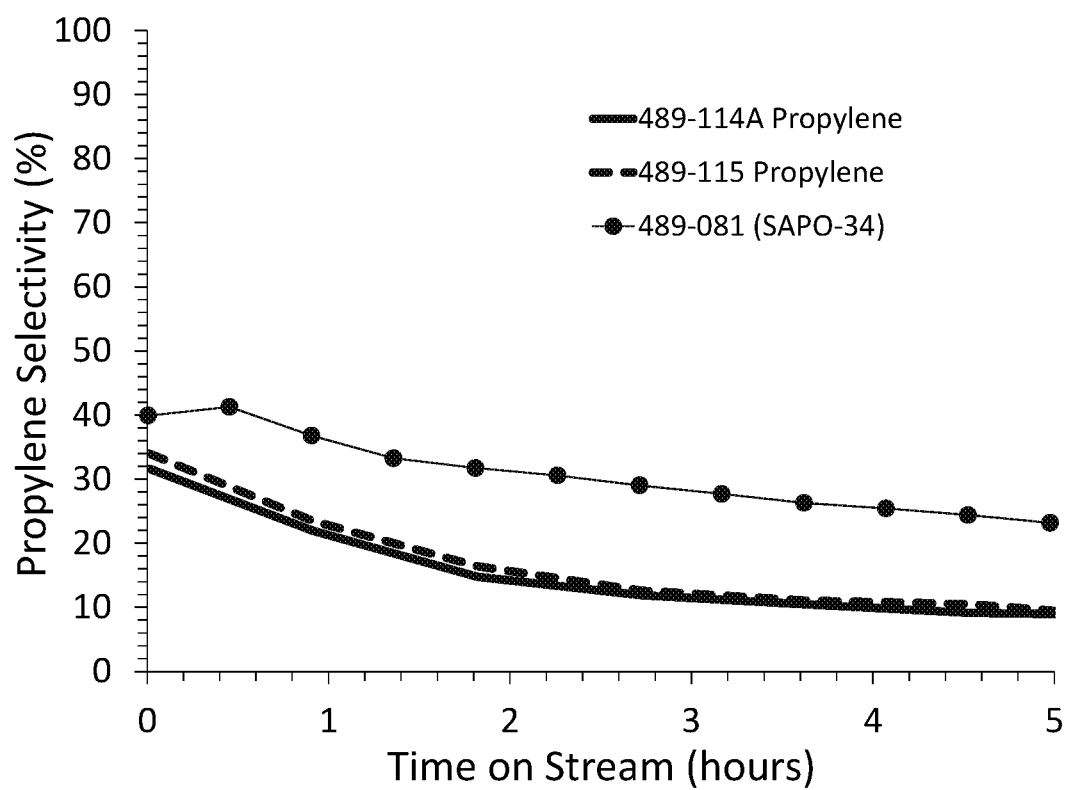
FIG. 5 is a graphical representation showing the time on stream selectivity of propylene formation for SSZ-13 catalyst samples A and B and the comparative SAPO-34 catalyst during the conversion of chloromethane to olefins at a WHSV of 2.7/hr and P of 0 MPa.

FIG. 3 is a graphical representation showing the time on stream conversion of chloromethane for SSZ-13 catalyst samples A and B as compared to a comparative SAPO-34 sample at a WHSV of 2.7/hr and a pressure of 0 MPa. The dashed line represents SSZ-13 catalyst A, the solid line represents SSZ-13 catalyst B, and the line with circular data markers represents SAPO-34. FIG. 4 is a graphical representation showing the time on stream selectivity of ethylene formation for SSZ-13 catalyst samples A and B and the comparative SAPO-34 catalyst during the conversion of chloromethane to olefins at a WHSV of 2.7/hr and P of 0 MPa. The solid line represents ethylene conversion for SSZ-13 catalyst A, the dashed line represent ethylene conversion for SSZ-13 catalyst B, the data line with circular data markers represents ethylene conversion for comparative catalyst SAPO-34. FIG. 5 is a graphical representation showing the time on stream selectivity of propylene formation for SSZ-13 catalyst samples A and B and the comparative SAPO-34 catalyst during the conversion of chloromethane to olefins at a WHSV of 2.7/hr and P of 0 MPa. The solid line represents propylene conversion for SSZ-13 catalyst A, the dashed line represent ethylene conversion for SSZ-13 catalyst B, the data line with circular data markers represents propylene conversion for comparative catalyst SAPO-34. From the data, the SSZ-13 catalysts of the present invention provided a higher conversion of methyl chloride (e.g., about 10% higher) than the SAPO-34 catalyst with ethylene and propylene selectivities similar to SAPO-34. Thus, the catalyst of the present invention provides a solution to the low conversion of alkyl halides to olefins when using SAPO-34 catalyst to convert alkyl halides to olefins.

The invention claimed is:

1. A method for converting an alkyl halide to an olefin, the method comprising contacting an aluminosilicate catalyst having a chabazite zeolite structure with a feed comprising an alkyl halide under reaction conditions sufficient to produce an olefin hydrocarbon product comprising C$_2$-C$_4$ olefins, wherein the feed is substantially free of oxygenates, wherein the aluminosilicate catalyst is SSZ-13.

2. The method of claim 1, wherein the feed comprises at least 50 wt. %, at least 75 wt. %, at least 80 wt. %, or at least 90 wt. % alkyl halide.

3. The method of claim 1, wherein the aluminosilicate catalyst has a silica (SiO$_2$) to alumina (Al$_2$O$_3$) mole ratio (SAR) of less than 100:1.

4. The method of claim 3, wherein the SAR is 30:1 to 50:1.

5. The method of claim 3, wherein the SAR is 65:1 to 85:1.

6. The method of claim 1, wherein the feed stream includes less than 5 wt. % alcohol.

7. The method of claim 6, wherein the alcohol is methanol or ethanol.

8. The method of claim 1, wherein the feed stream includes less than 5 wt. % oxygenates.

9. The method of claim 1, wherein the alkyl halide is a methyl halide.

10. The method of claim 9, wherein the methyl halide is methyl chloride, methyl bromide, methyl fluoride, or methyl iodide, or any combination thereof.

11. The method of claim 10, wherein the methyl halide is methyl chloride.

12. The method of claim 1, wherein the reaction occurs in a fluid catalytic cracking (FCC) reactor or fluidized circulating bed reactor.

13. The method of claim 1, wherein the reaction conditions include a temperature from 300° C. to 500° C., a pressure of 0.5 MPa or less, and a weighted hourly space velocity (WHSV) of 0.5 to 10 h$^{-1}$.

14. The method of claim 13, wherein the maximum combined selectivity of ethylene and propylene is at least 65% or 65% to 75%, wherein the maximum combined space time yield of ethylene and propylene is at least 1/hr or 1/hr to 3/hr, and/or wherein the maximum conversion of alkyl halide is at least 70% or 80% to 100%.

15. The method of claim 14, wherein the maximum selectivity of ethylene is 50% to 70% and the maximum selectivity of propylene is 60% to 80%.

16. The method of claim 1, further comprising collecting or storing the produced olefin hydrocarbon product.

17. The method of claim 1, further comprising using the produced olefin hydrocarbon product to produce a petrochemical or a polymer.

18. The method of claim 1, further comprising regenerating used/deactivated catalyst in a continuous process such as a fluid catalytic cracking (FCC)-type process or reactor or a circulating catalyst bed process or reactor.

19. A system for producing olefins, the system comprising:
an inlet for a feed comprising an alkyl halide, wherein the feed is substantially free of oxygenates;
a reaction zone that is configured to be in fluid communication with the inlet, wherein the reaction zone comprises the feed and an aluminosilicate catalyst having a chabazite zeolite structure, wherein the aluminosilicate catalyst is SSZ-13; and
an outlet configured to be in fluid communication with the reaction zone to remove an olefin hydrocarbon product from the reaction zone.

20. A method for converting an alkyl halide to an olefin, the method comprising contacting an aluminosilicate catalyst having a chabazite zeolite structure with a feed comprising an alkyl halide under reaction conditions sufficient to produce an olefin hydrocarbon product comprising C$_2$-C$_4$ olefins, wherein the feed is substantially free of oxygenates, wherein the aluminosilicate catalyst has a silica (SiO$_2$) to alumina (Al$_2$O$_3$) mole ratio (SAR) of less than 100:1.

* * * * *